Figure 1:
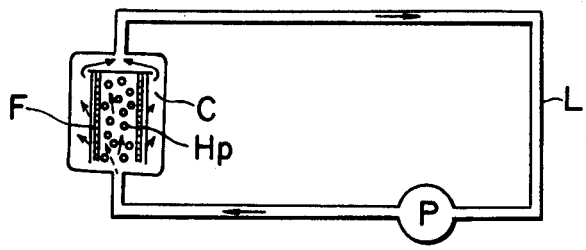

United States Patent [19]

Funakoshi et al.

[11] 4,113,853
[45] Sep. 12, 1978

[54] HAPTOGLOBIN INSOLUBILIZED BY BEING FIXED IN FIBRIN

[75] Inventors: Satoshi Funakoshi, Katano; Takao Oomura, Toyonaka, both of Japan

[73] Assignee: The Green Cross Corporation, Osaka, Japan

[21] Appl. No.: 813,419

[22] Filed: Jul. 6, 1977

[30] Foreign Application Priority Data

Aug. 27, 1976 [JP] Japan .................. 51-102763

[51] Int. Cl.² ............ A61K 31/74; A61K 35/14; A61K 37/04
[52] U.S. Cl. ........................... 424/78; 424/81; 424/101; 424/177
[58] Field of Search ............ 424/177, 101, 81, 78

[56] References Cited
PUBLICATIONS

Tsapis et al – Chem. Abst. vol. 85 (1976) p. 15677e.
Regoeczi – Chem. Abst. vol. 68 (1968) p. 101,852p.

*Primary Examiner*—Sam Rosen
*Attorney, Agent, or Firm*—Cushman, Darby & Cushman

[57] ABSTRACT

Because of its large hemoglobin-binding capacity, high physical strength, and ability to be reused on regeneration, the active haptoglobin fixed and insolubilized by embedding into or by chemical interlinking with fibrin is useful for absorbing and removing free hemoglobin liberated in the circulating blood plasma when it is included in an extracorporeal blood circulation system such as an artificial cardiopulmonary system.

28 Claims, 3 Drawing Figures

HAPTOGLOBIN INSOLUBILIZED BY BEING FIXED IN FIBRIN

This invention relates to water-insoluble fixed haptoglobin preparations for medical use.

Haptoglobin (hereinafter some times referred to as Hp) is a blood plasma protein having a molecular weight of 86,000 to 400,000 and plays an important role in the metabolism of hemoglobin liberated in the blood. When liberated excessively in the blood, the hemoglobin (hereinafter some times referred to as Hb) is excreted into the urine through the renal tubules, resulting in not only an iron loss but also disorders of the renal tubules. Haptoglobin has important functions in the recovery of iron and the prevention of renal disorders, because it binds selectively and firmly to hemoglobin in vivo, forming a hemoglobin-haptoglobin complex which is easily accepted chiefly by parenchymal cells of liver and metabolized therein.

Hemolysis poses an important problem today, because when hemolysis, i.e. liberation of hemoglobin, is induced by incompatible transfusion, severe burns, cardiac surgery, hemolytic diseases, and the like, the patient frequently suffers from accompanied renal disorders leading to renal insufficiency which can be fatal. The present inventors have paid special attention to the possible use of haptoglobin in treating such renal disorders due to hemolysis and developed a method for preparing highly purified haptoglobin [Japanese Patent Application "Kokai" (Laid-open) No. 77,516/75; British Pat. No. 1,426,039; West German Patent Application No. p. 2,409,650 (Laid-open); French Patent Application (Laid-open) 2,251,314] and have supplied injectable haptoglobin preparations for use in treatment of the causes of the above-noted renal disorders. When a haptoglobin preparation is administrated intravenously, the haptoglobin combines with liberated hemoglobin and thus serves to normalize the metabolic excretion of hemoglobin.

On the other hand, rapid advances have recently been made in the technique of treating patients by using an extracorporeal blood circulation system such as an artificial cardiopulmonary system or an artificial kidney. However, prolonged blood circulation through such an extracorporeal system tends to induce hemolysis, liberating hemoglobin. The liberated hemoglobin often causes renal disorders which make difficult the continuation of the treatment with the extracorporeal circulation system. Treatment with a haptoglobin preparation is effective also in the case of hemolysis caused by the continued extracorporeal circulation. However, haptoglobin preparation once administered into a living body can not be recovered, that is to say, the haptoglobin preparation can not be reused. Moreover, if the haptoglobin preparation is injected into a living body, the hemoglobin combines with the haptoglobin, that is, a hemoglobin-haptoglobin complex (hereinafter sometimes referred to as Hb-Hp) is carried to the liver and metabolized therein, thereby imposing too heavy a burden on a patient with declined renal function. Accordingly, intravenous injection of a haptoglobin preparation into such a patient is impractical.

There had been suggested a method for removing liberated hemoglobin from the blood utilizing the technique of the so-called affinity chromatography, which comprises bonding haptoglobin to a carrier comprising agarose to fix and insolubilize the haptoglobin and using the resulting product as adsorbent [Michel Klein and Constantin Mihaesco, Biochemical and Biophysical Research Communications, Vol. 52, No. 3 (1973)]. One of the present inventors and his other associates advanced, in the therapeutic sense, the above technique and invented a method and device, which may be called a blood filtration device, for removing liberated hemoglobin by allowing the hemoglobin in circulating blood to bind to the insolubilized haptoglobin supported on various carriers and included in an extracorporeal circulating system such as, for example, an artificial cardiopulmonary system. The inventors thus succeeded in removing the hemoglobin directly from the body without imposing any burden in the liver [Japanese Patent Application "Kokai" (Laid-open), Nos. 105,186/76, 79,717/76, and 79,718/76]. However, all of these water-insoluble fixed haptoglobin preparations disclosed in prior inventions on a practical base were not so highly rateable, in view of the amount of fixed Hp, Hb-binding capacity, physical strength, and performance after regeneration.

An object of the present invention is to provide an insolubilized haptoglobin preparation in which the active haptoglobin content is high.

Another object of the present invention is to provide an insolubilized haptoglobin preparation having a high hemoglobin-binding capacity.

Another object of the present invention is to provide an insolubilized haptoglobin preparation having a physical strength sufficient to use it as an adsorbent of hemoglobin in an extracorporeal circulating system.

A further object of the present invention is to provide an insolubilized haptoglobin having a high performance after regeneration when used as an adsorbent of hemoglobin in an extracorporeal circulating system.

The present inventors conducted extensive studies to achieve the above objects and, as a result, found that fibrin is especially effective as the carrier for fixing haptoglobin. Based on this finding, the present invention has been accomplished.

According to the present invention, there is provided an insolubilized haptoglobin preparation comprising fibrin and active haptoglobin insolubilized by being fixed to said fibrin.

There is further provided, according to the present invention, a method of preparing an insolubilized haptoglobin preparation, which comprises reacting fibrinogen, haptoglobin, thrombin, and bifunctional compound with one another.

Because of its high hemoglobin-binding capacity and ability to maintain its activity for a long period of continuous use, the fixed haptoglobin preparation according to this invention is far more suitable for practical uses compared with conventional fixed Hp preparations or the preparations for injection.

The method for preparing insolubilized haptoglobin according to this invention is carried out by simply embedding haptoglobin in fibrin, following the technique used in insolubilizing an enzyme, or by allowing haptoglobin and fibrin or fibrinogen to react with a bifunctional compound capable of reacting with these substances and interlinking them and then, if fibrinogen is used, allowing the reaction product to react with thrombin to convert the fibrinogen moiety into the fibrin moiety.

The type of haptoglobin for use in this invention is subject to no special limitation because it varies depending upon the intended use of the preparation. In the case where the haptoglobin preparation is intended to be used in a hemoglobin removing device included in an extracorporeal circulation system, it is desirable to use an injectable purified haptoglobin of human origin provided by the method for preparing an aqueous solution of haptoglobin according to the aforesaid prior invention (loc. cit.).

Fibrinogen is a substance which changes into water-insoluble fibrin by the action of thrombin. The fibrinogen used in the present reaction is not limited to any special type, because it depends on where the haptoglobin preparation is intended to be used. If the preparation is to be used in an extracorporeal circulation system, a fibrinogen of human origin is preferred. Such a fibrinogen is provided by known methods such as, for example, Cohn's cold ethanol fractionation method, fraction I being a suitable source. The haptoglobin, fibrinogen, and thrombin for use in the reaction are preferably pretreated to inactivate the hepatitis virus by known methods such as, for example, heat treatment and ultraviolet irradiation. By selecting starting materials which have undergone such a treatment, there is obtained a product having no risk of hepatitis virus infection.

The interlinking agents for use in the present invention are bifunctional compounds known as insolubilizing interlinking agents for enzymes, such as glutaraldehyde, hydrazine, ethylenediamine, methylene dibromide, bisdiazo-o-dianisidine, bisdiazobenzidine, and carbodiimide. Of these, particularly preferred are glutaraldehyde and carbodiimide because of the high interlinking efficiency and sufficient retention of Hb-binding capacity of the product.

The reactions involving haptoglobin, fibrinogen, bifunctional compound, and thrombin according to this invention are carried out in an aqueous medium. The reaction sequence among reactants to not critical so long as the interlinking between fibrinogen or fibrin and haptoglobin is effected. Similar results are obtained by reacting a bifunctional compound with a mixture of fibrinogen and haptoglobin and then reacting thrombin with the reaction mixture to convert the fibrinogen moiety to the fibrin moiety; by first converting fibrinogen into fibrin by the action of thrombin and then allowing a mixture of the resultant fibrin and haptoglobin to react with a bifunctional compound; by reacting fibrin with a mixture of haptoglobin and a bifunctional compound; or by reacting haptoglobin with a mixture of fibrin and a bifunctional compound. However, the most preferable procedure consists in allowing the four reactants fibrinogen, haptoglobin, bifunctional compound, and thrombin to react simultaneously with one another.

The functional groups of the functional compound combine with the functional groups of amino acids in fibrin and haptoglobin, such as, for example, amino groups, carboxyl groups and phenolic groups, thus forming an insoluble fibrin-haptoglobin bonded product.

The reaction conditions are as follows: the weight ratio of fibrinogen to haptoglobin is 0.5–3.0:1; the amount of thrombin to be added in order to convert fibrinogen into fibrin is 30–100 NIH units for 1 g of fibrinogen; a suitable amount of a bifunctional compound to be added is 1–47 mM, preferably not exceeding a maximal amount of 50 mM; the reaction temperature can be 0° to 40° C. throughout, but the desirable temperature of interlinking is 0° to 10° C., preferably 0° to 5° C., and that of conversion to fibrin is 20° to 40° C., preferably 28° to 32° C.; the desirable pH of the reactant mixture is in the range near the neutral point (i.e. pH 6 to 8); a suitable reaction medium is physiological saline solution or 0.1 molar phosphate buffer solution; and the reaction time is about 30 minutes to about 3 hours, although in most cases 2 hours are sufficient for completion of the reaction.

The simple embedding of haptoglobin in fibrin, which is another procedure for preparing an insolubilized haptoglobin of this invention, can be performed by mixing fibrinogen and haptoglobin in an aqueous medium and adding thrombin to the resulting mixture to convert the fibrinogen into fibrin. The amount of starting materials to be used and the reaction conditions are about the same as mentioned above.

The insolubilized haptoglobin preparation thus obtained, especially that insolubilized by interlinking, has high practical valuue with respect to the amount of fixed Hp, Hb-binding capacity, physical strengths, and reusability, as shown in Experimental Examples 1 to 3. On comparing the results obtained in these Experimental Examples with one another, it was found that as compared with conventional preparations, the haptoglobin preparation of this invention is about 2 to 10 times as large in the amount of fixed haptoglobin, about 2 to 9 times as large in Hb-binding capacity, and about 2 to 6 times as high in physical strengths; and that it combines with about 3 to 7 times as much Hb when used repeatedly. The amount of fixed Hp is approximately 100 to 600 mg/g on dry basis and the Hb-binding capacity is about 20 to 115 mg Hb/g on dry basis.

When the present haptoglobin preparation is integrated into an extracorporeal circulation system as a filter bed in the form of granules in order to keep the preparation from being carried away by the blood streams it is useful for prophylaxis and therapy of hemolytic renal disorders caused by the continual use of the extracorporeal circulation system. The minimum size of the granules is more than about 40 $\mu$, although the smaller the better in order to bind efficiently the hemoglobin.

The present preparation can be further improved in physical strength and Hb-binding capacity by enlarging the surface area of the fibrin by forming it into a membrane supported on an auxiliary carrier. A suitable auxiliary carrier are heat-resistant fibers in the form of filaments, films, or nettings. The heat-resistant fibers include natural and synthetic fibers, from which a choice is made according to the intended use of the haptoglobin preparation. Examples of suitable fibers are fibers of the polyolefin type, polyacrylonitrile type, polyester type, polyacetate type, and polyvinyl alcohol type (vinylon ®).

The insolubilized haptoglobin supported on an auxiliary carrier may be prepared with high efficiency by either insolubilizing membraneous fibrinogen supported on the auxiliary carrier with thrombin, and then allowing the insolubilized fibrin membrane, haptoglobin, a bifunctional compound, and the auxiliary carrier to react simultaneously with one another, or allowing directly a mixture comprising fibrinogen, haptoglobin, thrombin, and a bifunctional compound to react simultaneously with one another in the presence of an auxiliary carrier. The bifunctional compound reacts also with active groups of the auxiliary carrier to yield an active insolubilized haptoglobin having high physical strength.

Since the present haptoglobin preparation combines with hemoglobin liberated in an aqueous medium, it is useful not only for the removal of hemoglobin from an extracorporeal circulation system, but also for general blood analysis; it is also useful as a carrier in performing fractionation of the plasma on account of its combination selectivity and, in addition, adaptable is to the recovery of hemoglobin.

The invention is illustrated below with reference to the Examples, but the invention is not limited to the Examples.

In the Examples, the amounts of insolubilized haptoglobin were estimated by calculation from the amounts of unfixed haptoglobin recovered from the washings after fixation of haptoglobin to fibrin, as assayed by the method of a single radial immunodiffusion [G. Mancini, A.O. Carbonara, and T. F. Heremans, Immunochem., 2, 235 (1965)]. Unless otherwise indicated, the Hb-binding capacities were obtained by packing a column with the insolubilized haptoglobin, passing an excess of a hemoglobin solution through the column to combine the hemoglobin with the haptoglobin, assaying the amount of residual hemoglobin in the solution by the method of cyanmethemoglobin [E. J. Kampen, Clin. Chim. Acta, 6, 538 (1961)], and calculating the amount of combined hemoglobin.

The accompanying drawings show the apparatus used in and the results obtained from comparative examinations conducted on the present insolubilized haptoglobin, conventional insolubilized haptoglobin, and haptoglobin insolubilized by the known enzyme-immobilizing method.

FIG. 1 is a schemtic representation of the liquor circulating apparatus employed in measuring physical strengths of the insolubilized haptoglobin.

Figure 2:
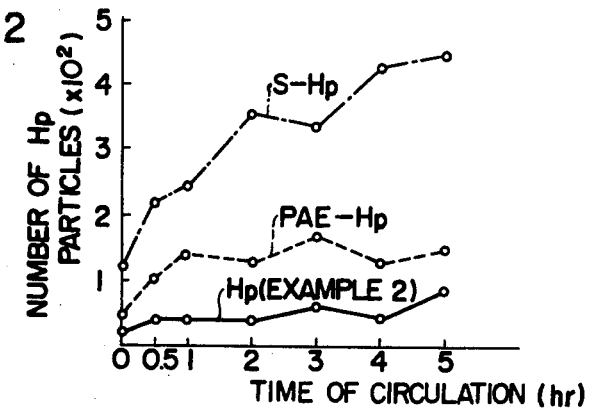

In FIG. 2 are shown the results of the measurements. Explanations about the apparatus and test results are given in Experimental Example 2 below.

Figure 3:
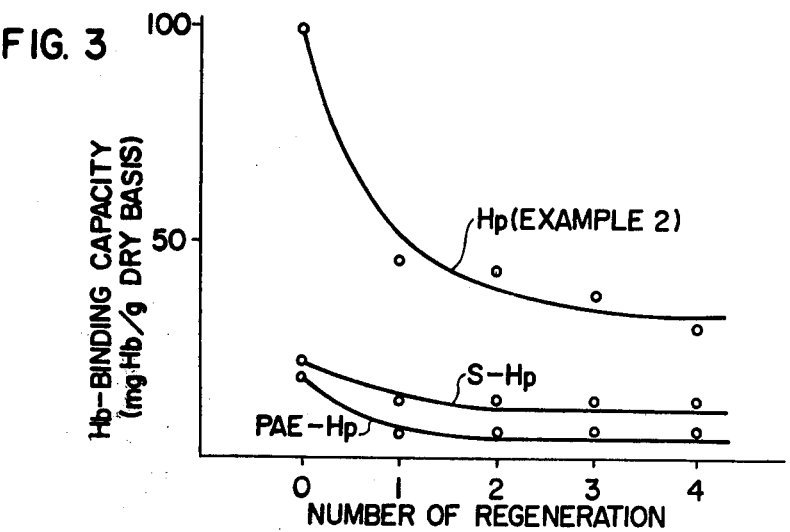

FIG. 3 shows the results of regeneration tests conducted on the insolubilized haptoglobin, as explained in Experimental Example 3.

EXAMPLE 1

To 1 liter of a 2.0-%(W/V) solution (pH 7; 0.1 M phosphate buffer solution) of purified fibrinogen recovered from human plasma, were added 20 g of purified haptoglobin recovered from human plasma, followed by 200 ml containing thrombin of 10 NIH units/ml. The mixture was left standing at 30° C. for 2 hours to sufficiently coagulate the fibrin. After washing, the mass of fibrin was lyophilized and the resulting granules were collected as uniform particles (50 to 150 $\mu$). The granules were washed twice with the physiological saline solution to obtain 38 g of a fixed haptoglobin preparation. On the first washing, the fixed haptoglobin content was 390 mg/g on a dry basis and on the second washing it was 100 mg/g on a dry basis and the Hb-binding capacity was about 20 mg Hb/g on a dry basis.

EXAMPLE 2

To 2 liters of a 2.0-%(W/V) solution (pH 7, 0.1 M phosphate buffer solution) of purified human fibrinogen, were added 20 g of purified human haptoglobin, followed by glutaraldehyde, with stirring, until the final concentration thereof became 10 mM. The mixture was stirred at 0° to 5° C. for 20 minutes. After addition of 200 ml of thrombin containing 10 NIH units/ml, the mixture was left standing at 30° C. for 2 hours. The resulting mass of fibrin was washed, lyophilized and the resulting particles were screened to uniform size (50 to 150 $\mu$). After washing and drying, there were obtained 52 g of a fixed haptoglobin preparation. The fixed haptoglobin content was about 384 mg/g on a dry basis and the Hb-binding capacity was about 115 mg Hb/g on a dry basis. There was no appreciable difference in the fixed haptoglobin content after the first and second washing.

EXAMPLE 3

A piece of nylon plain gauze of about 100 mesh (ASTM) cut to 165 mm × 200 mm was welded at both ends to stainless steel wire and rolled into a coil. The coiled nylon gauze was placed in a Pyrex glass column having a 90 ml capacity (28 mm in internal diameter and 145 mm in height) and wetted with a sufficient amount of a thrombin solution containing 20 NIH units/ml. After removal of the excess thrombin solution, a mixture comprising 20 ml of a 2.0-%(W/V) solution of purified human fibrinogen (dissolved in physiological saline solution), 200 mg of purified human haptoglobin, and 5 mM of glutaraldehyde was quickly poured into the column.

The temperature of the fixing apparatus and the reaction liquor was kept at 5° C. during the above procedure. After the mixed solution had been sufficiently distributed throughout the nylon gauze, the excess solution was removed. The column was kept rotating at 30° C. for 2 hours to deposit fibrin thus formed on the nylon gauze. The fibrin was allowed to shrink sufficiently by being left standing overnight at 4° C. and then washed well with the physiological saline solution.

The thus obtained fixed haptoglobin showed a fixed haptoglobin content of 180 mg/fixed column and a Hb-binding capacity of 65 mg/fixed column.

EXAMPLE 4

The procedure of Example 3 was repeated, except that 10 mM of carbodiimide were used in place of the glutaraldehyde. The results were not appreciably different from those obtained in Example 3. The fixed haptoglobin content was 175 mg/fixed column and the Hb-binding capacity was 62 mg Hb/fixed column.

EXPERIMENTAL EXAMPLE 1

The fixed haptoglobin preparations obtained in Examples 1 and 2 and conventional preparations including haptoglobin fixed to polyacrylamide gel copolymerized with active ester (PAE-Hp) and haptoglobin fixed to Sepharose ® (agarose, sold by Pharmacia Co., Ltd., Sweden) (S-Hp) were compared as to the fixed Hp content and Hb-binding capacity. PAE-Hp was prepared by the reaction of purified human haptoglobin with polyacrylamide gel copolymerized with active ester obtained according to the method of Schnaar and Lee [Biochem., 14, 1535 (1975)]. S-Hp was prepared according to the method of Klein and Mihaesco (loc. cit.). The haptoglobin used was of a purified grade of human origin and the amount was 20 g.

|  | Fixed Hp content (mg/g on dry basis) | Hb-binding capacity (mg Hb/g on dry basis) |
| --- | --- | --- |
| Insolubilized Hp of Example 1 (embedded in fibrin) | 100 | 20 |
| Insolubilized Hp of Example 2 (fibrin-glutaraldehyde interlinking) | 384 | 115 |

|  | Fixed Hp content (mg/g on dry basis) | Hb-binding capacity (mg Hb/g on dry basis) |
|---|---|---|
| S-Hp | 76 | 14 |
| PAE-Hp | 60 | 13 |

Experimental EXAMPLE 2

The insolubilized haptoglobin preparations other than that of Example 1 used in Experimental Example 1 were compared with one another for physical strength against disintegration caused by the liquid flow.

The experiment was conducted on 30 ml of each insolubilized haptoglobin preparation packed in a Barrier-filter (made by Johnson and Johnson Co.) having a 50 ml capacity which was set in a circulation apparatus shown in FIG. 1. The circulation apparatus consisted of a chamber C enclosing the Barrier ® extracorporeal blood filter F, an endless pipeline L connected to the chamber C, and a pump P set in the pipeline L. One liter of the physiological saline solution was circulated through the pipeline L by means of the pump P at a flow rate of 500 ml/0.05 cm$^3$/minute. Samples of the circulating saline solution were withdrawn at an interval of 1 hour from the beginning of circulation till 5 hours of circulation had been completed. The number of particles of insolubilized haptoglobin preparation appearing in the sample on account of disintegration was determined by means of a hematometer at a magnification of 50. The pore diameter of the Barrier ® extracorporeal blood filter was 20 to 40 $\mu$, while the insolubilized haptoglobin preparation was screened to 50-150 $\mu$. The variation with time in the number of haptoglobin particles was as shown in FIG. 2, wherein the ordinate indicates the number of Hp particles appearing in 1 ml of the physiological saline solution and the abscissa indicates the time of circulation. It is seen from FIG. 2 that the physical strength of the insolubilized haptoglobin preparation obtained in Example 2 is about 2 to 7 times that of conventional preparations.

Experimental EXAMPLE 3

Reusability of each of the same insolubilized haptoglobin preparations prepared in Experimental Example 1 was tested for comparison. The experiment was conducted in the following manner:

After following 5 ml of the insolubilized haptoglobin to combine with enough hemoglobin, the hemoglobin-loaded preparation was admixed with 30 ml of an aqueous 5 M MgCl$_2$ solution (pH about 4.3) to split completely the Hp-Hb bond and the amount of hemoglobin liberated in the solution was determined in order to calculate the Hb-binding capacity of the insolubilized haptoglobin. The haptoglobin regenerated on liberation of the hemoglobin was again allowed to combine with a sufficient amount of hemoglobin and then treated as mentioned above to liberate hemoglobin. The above treatment was further repeated to examine the change in Hb-binding capacity with the repetition of the treatment.

The results obtained were as shown in FIG. 3, wherein the ordinate indicates the residual Hb-binding capacity (mg Hb/g on dry basis) and the abscissa the number of regenerations. It is seen from FIG. 3 that the haptoglobin preparation obtained in Example 2 retained, after the fourth regeneration, a Hb-binding capacity of about 4 to 8 times that of conventional preparations.

What is claimed is:

1. An insolubilized haptoglobin comprising fibrin and active haptoglobin insolubilized by being fixed in said fibrin, said fixing being effected by interlinking through an interposed bifunctional compound.

2. The insolubilized haptoglobin of claim 1, characterized by containing about 100 to about 600 mg of the fixed haptoglobin per gram.

3. The insolubilized haptoglobin of claim 1, characterized by having a hemoglobin-binding capacity of about 20 to about 115 mg Hb/g.

4. The insolubilized haptoglobin of claim 1, characterized by being freed from the risk of hepatitis virus infection.

5. The insolubilized haptoglobin of claim 1, characterized by having a grain diameter of 50 to 150 $\mu$.

6. The insolubilized haptoglobin of claim 1, wherein the fibrin and haptoglobin are of human origin.

7. The insolubilized haptoglobin of claim 1, wherein the interposed bifunctional compound is glutaraldehyde or carbodiimide.

8. The insolubilized haptoglobin of claim 1, characterized by being supported on a carrier.

9. The insolubilized haptoglobin of claim 8, wherein the synthetic fiber is a member selected from the group consisting of polyolefins, polyacrylonitriles, polyesters, polyacetates, and polyvinyl alcohol.

10. A method for preparing insolubilized haptoglobin, which comprises allowing fibrinogen, haptoglobin, thrombin, and a bifunctional compound to react with one another.

11. The method according to claim 10, wherein both the fibrinogen and the haptoglobin are of human origin.

12. The method according to claim 10, wherein the bifunctional compound is a member selected from the group consisting of glutaraldehyde and carbodiimide.

13. The method according to claim 12, wherein the bifunctional compound is glutaraldehyde.

14. The method according to claim 12, wherein the bifunctional compound is carbodiimide.

15. The method according to claim 10, wherein the reaction is carried out in an aqueous medium at pH 6-8.

16. The method according to claim 10, wherein the reaction is carried out using a reactant ratio of 1 g of haptoglobin, about 0.5 to about 3.0 g of fibrinogen, 1 to 47 mM of a bifunctional compound, and 15 to 300 NIH units of thrombin.

17. The method according to claim 10, wherein the reaction is carried out at 0° to 40° C.

18. The method according to claim 10, wherein the reaction is carried out in such a sequence that at first the bifunctional compound is reacted with a mixture of fibrinogen and haptoglobin and then the reaction mixture is reacted with thrombin.

19. The method according to claim 10, wherein the reaction is carried out in such a sequence that at first thrombin is reacted with fibrinogen and then the resulting fibrin and haptoglobin are reacted with a bifunctional compound.

20. The method according to claim 10, wherein the reactants are allowed to react simultaneously with one another.

21. The method according to claim 18, wherein the reaction with thrombin is carried out at a temperature of 20° to 40° C.

22. The method according to claim 19, wherein the reaction with thrombin is carried out at a temperature of 20° to 40° C.

23. The method according to claim 18, wherein the reaction with the bifunctional compound is carried out at a temperature of 0° to 10° C.

24. The method according to claim 19, wherein the reaction with the bifunctional compound is carried out at a temperature of 0° to 10° C.

25. The method according to claim 10, wherein the reaction is carried out in the presence of an auxiliary carrier.

26. The method according to claim 25, wherein the auxiliary carrier is natural or synthetic fiber.

27. The method according to claim 26, wherein the synthetic fiber is a member selected from the group consisting of polyolefins, polyacrylonitriles, polyesters, polyacetates, and polyvinyl alcohol.

28. An insolubilized haptoglobin comprising fibrin and active haptoglobin insolubilized by being fixed in said fibrin, said insolubilized haptoglobin being supported on a natural or synthetic fiber carrier.

* * * * *